United States Patent [19]

Beriger

[11] 4,006,228
[45] Feb. 1, 1977

[54] PESTICIDALLY ACTIVE THIO- AND DITHIOPHOSPHORIC ACID ESTERS

[75] Inventor: Ernst Beriger, Allschwil, Switzerland

[73] Assignee: Ciba-Geigy Corporation, Ardsley, N.Y.

[22] Filed: Sept. 10, 1975

[21] Appl. No.: 612,123

[30] Foreign Application Priority Data

Sept. 20, 1974 Switzerland ............... 12794/74
July 17, 1975 Switzerland ............... 9340/75

[52] U.S. Cl. ............................ 424/212; 260/941
[51] Int. Cl.² .................. A01N 9/36; C07F 9/02
[58] Field of Search ................ 260/941; 424/212

[56] References Cited

UNITED STATES PATENTS 3,784,589  1/1974  Large ........................ 260/941
3,883,618  5/1975  Oswald et al. ............... 260/941

Primary Examiner—V. D. Turner
Attorney, Agent, or Firm—Harry Falber

[57] ABSTRACT

Thio- and dithiophosphoric acid esters of the formula I

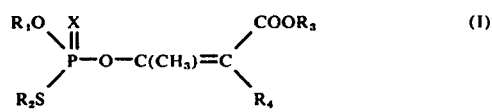

wherein
$R_1$ is methyl or ethyl,
$R_2$ is $C_3$–$C_5$-alkyl,
$R_3$ is $C_1$–$C_5$-alkyl, $C_3$–$C_5$-alkenyl, $C_3$–$C_5$-alkynyl, benzyl, α-phenethyl or β-phenethyl,
$R_4$ is phenyl or a group of the formula —$CH_2$-$COOR_3$ wherein $R_3$ has the meaning given above and
X is oxygen or sulphur are pesticidal in particular acaridal or insecticidal agents.

7 Claims, No Drawings

PESTICIDALLY ACTIVE THIO- AND DITHIOPHOSPHORIC ACID ESTERS

The present invention relates to new pesticidally active thio- and dithiophosphoric acid esters, processes for the production of these esters, and to compositions and processes for controlling pests employing the new as active substances.

The new thio- and dithiophosphoric acid esters of the invention correspond to the formula I $$\begin{array}{c} R_1O \\ \diagdown \\ R_2S \end{array} \overset{X}{\underset{\parallel}{P}} -O-C(CH_3)=C \begin{array}{c} COOR_3 \\ \diagdown \\ R_4 \end{array} \quad (I)$$

wherein
- $R_1$ represents a methyl or ethyl radical,
- $R_2$ represents a $C_3$–$C_5$-alkyl radical,
- $R_3$ represents a $C_1$–$C_5$-alkyl, $C_3$–$C_5$-alkenyl, $C_3$–$C_5$-alkynyl or benzyl radical or an α- or β-phenethyl radical,
- $R_4$ represents a phenyl radical, or a group of the formula —$CH_2$-$COOR_3$ wherein $R_3$ has the already given meaning, and
- X stands for an oxygen or sulphur atom.

Alkyl, alkenyl and alkynyl radicals in formula I can be branched-chain or straight-chain. Alkyl radicals denoted by $R_2$ and $R_3$ are the methyl, ethyl, n-propyl, isopropyl, n-butyl, isobutyl, sec.-butyl and tert.-butyl radicals as well as the n-pentyl radical and isomers thereof; and alkenyl or alkynyl radicals denoted by $R_2$ and $R_3$ are, e.g., allyl, methallyl, 1,2-dimethylallyl, propargyl, 1-methyl-2-propynyl, 1,1-dimethyl-2-propynyl and 1-methyl-1-ethyl-2-propynyl.

Of particular importance on account of their action against pests, especially against insects and members of the order Acarina, are thio- and dithiophosphoric acid esters of the above-mentioned formula I wherein
- $R_1$ represents an ethyl radical,
- $R_2$ represents a $C_3$–$C_5$-alkyl radical,
- $R_3$ represents a $C_1$–$C_5$-alkyl radical,
- $R_4$ represents a phenyl or ($C_2$–$C_6$-alkoxycarbonyl)-methyl radical, and
- X represents an oxygen or sulphur atom, and of these the preferred esters are those wherein
- $R_1$ represents an ethyl radical,
- $R_2$ represents an n-propyl radical,
- $R_3$ represents a methyl, ethyl or isopropyl radical,
- $R_4$ represents a phenyl, methoxycarbonylmethyl or ethoxycarbonylmethyl radical, and
- X represents an oxygen or sulphur atom.

The new compounds of the formula I are obtained by methods known per se; for example, a. by reacting a compound of the formula II $$CH_3-CO-CH \begin{array}{c} COOR_3 \\ \diagdown \\ R_4 \end{array} \quad (II),$$

in the presence of an acid-binding agent, with a phosphoric acid halide of the formula III $$\begin{array}{c} R_1O \\ \diagdown \\ R_2S \end{array} \overset{X}{\underset{\parallel}{P}} -Hal \quad (III);$$

b. by reacting a compound of the formula IV $$\begin{array}{c} Hal \\ \diagdown \\ Hal \end{array} \overset{X}{\underset{\parallel}{P}} -O-C(CH_3)=C \begin{array}{c} COOR_3 \\ \diagdown \\ R_4 \end{array} \quad (IV)$$

firstly with an alcohol of the formula V
$$R_1 - OH \quad (V)$$
and subsequently with a mercaptan of the formula VI
$$R_2 - SH \quad (VI),$$

or firstly with a mercaptan of the above formula VI and subsequently with an alcohol of the above formula V;

c. by reacting potassium or sodium hydrosulphide with a compound of the formula VII $$\begin{array}{c} R_1O \\ \diagdown \\ R_2O \end{array} \overset{S}{\underset{\parallel}{P}} -O-C(CH_3)=C \begin{array}{c} COOR_3 \\ \diagdown \\ R_4 \end{array} \quad (VII)$$

and reacting the resulting compound of the formula VIII $$\begin{array}{c} R_1O \\ \diagdown \\ ZS \end{array} \overset{S}{\underset{\parallel}{P}} -O-C(CH_3)=C \begin{array}{c} COOR_3 \\ \diagdown \\ R_4 \end{array} \quad (VIII),$$

wherein Z represents a potassium or sodium atom, with an organohalide of the formula IX
$$R_2 - Hal \quad (IX).$$

The substituents $R_1$, $R_2$, $R_3$, $R_4$ and X in the formulae II to IX have the meanings already given under the formula I, while "Hal" stands for a halogen atom, especially a chlorine or bromine atom. Only compounds of the formula I wherein X represents sulphur are obtainable by process (c).

The processes (a) and (b) are performed at a reaction temperature of between −10° and 100° C, particularly between 20° and 80° C, under normal or elevated pressure, and preferably in a solvent or diluent inert to the reactants. The process (c) is carried out at a reaction temperature of 0° to 130° C, under normal pressure and preferably in the presence of a suitable solvent or diluent.

Suitable solvents or diluents for these reactions are, e.g., ethers and ethereal compounds such as diethyl ether, dipropyl ether, dioxane, dimethoxyethane or tetrahydrofuran; amides such as N,N-di-alkylated carboxylic acid amides; aliphatic, aromatic as well as halogenated hydrocarbons, especially benzene, toluene, xylenes, chloroform or chlorobenzene; nitriles such as acetonitriles; DMSO; and ketones such as acetone or methyl ethyl ketone; and for process (c) also alcohols such as ethanol and isopropanol. Suitable acid-binding agents for process (a) are, in particular, tertiary amines such as trialkylamines, also hydroxides, oxides, carbamates and bicarbonates of alkali metals and alkaline-earth metals, as well as alkali metal alcoholates such as potassium t.butylate and sodium methylate.

The derivatives of the formulae II, III, V, VI and IX are known or can be produced by methods analogous to known methods.

Starting materials of the formulae IV and VII are obtainable, by a process analogous to the above-described process (a), from the corresponding compound of the formula II by the reaction of this, in the presence of an acid-binding agent, with compounds of the formula X and XI, respectively

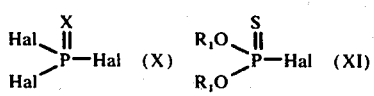

wherein $R_1$, X and "Hal" have the already given meanings.

The compounds of the formula I exhibit cis/trans isomerism. If therefore individual cis or trans starting materials are not used in the production process, cis/trans isomer mixtures are naturally obtained as reaction products. It is to be understood that the present invention relates both to the individual cis or trans isomers as well as to mixtures thereof.

The new compounds of the formula I are suitable for the control of pests, particularly for the control of insects and of members of the order Acarina. They can be used, e.g., against insects of the families: Tettigoniidae, Gryllidae, Gryllotalpidae, Blattidae, Reduviidae, Phyrrhocoridae, Cimicidae, Delphacidae, Aphididae, Diaspididae, Pseudococcidae, Scarabacidae, Dermestidae, Coccinellidae, Tenebrionidae, Chrysomelidae, Bruchidae, Tineidae, Noctuidae, Lymatriidae, Pyralidae, Culcidae, Tripulidae, Stomoxydae, Trypetidae, Muscidae, Calliphoridae and Pulicidae; as well as against acarids of the families: Tetranychidae and Dermanyssidae.

The compounds of the formula I are suitable, in particular, for the control of insects harmful to plants, especially insects which cause damage by eating for example to agricultural or horticultural crops or plants particularly to garden plants and fruit trees (e.g. for the control of aphids), as well as cotton crops (e.g. against *Spodoptera littoralis* or *Heliothis virescens*).

The acaricidal or insecticidal action can be appreciably broadened and adapted to suit given circumstances by the addition of other insecticides and/or acaricides. Suitable additives are, e.g., the following active substances: org. phosphorus compounds; nitrophenols and derivatives thereof; formamidines; ureas; pyrethrin-like compounds; carbamates and chlorinated hydrocarbons.

The compounds of formula I can be used on their own or together with suitable carriers and/or additives. Suitable carriers and additives may be solid or liquid, and correspond to the substances common in formulation practice, such as natural and regenerated substances, solvents, dispersing agents, wetting agents, adhesives, thickeners, binders and/or fertilisers.

For application, the compounds of the formula I can be processed into the form of dusts, emulsion concentrates, granulates, dispersions, sprays or solutions, the formulation of these preparations being effected in a manner commonly known in practice. Also to be mentioned are cattle dips and spray races, in which aqueous preparations are used.

The compositions according to the invention are produced in a manner known per se by the intimate mixing and/or grinding of active substances of formula I with suitable carriers, optionally with the addition of dispersing agents or solvents which are inert to the active substances. The active substances can be obtained and used in the following forms:

solid preparations: dusts, scattering agents, granulates, coated granulates, impregnated granulates and homogeneous granulates, liquid preparations:
  a. water-dispersible active-substance concentrates: wettable powders, pastes or emulsions;
  b. solutions.

The content of active substance in the described preparations is between 0.1 and 95%; it is to be mentioned in this connection that in the case of application from an aeroplane, or by means of other suitable devices, even higher concentrations can be used.

The active substances of formula I can be formulated, for example, as follows:

Dusts:

The following substances are used in the preparation of (a) a 5% dust, and (b) a 2% dust:
  a. 5 parts of active substance, 95 parts of talcum;
  b. 2 parts of active substance, 1 part of highly dispersed silicic acid, 97 parts of talcum.

The active substances are mixed and ground with the carriers.

Granulate:

The following substances are used to produce a 5% granulate:

| | |
|---|---|
| 5 | parts of active substance, |
| 0.25 | part of epichlorohydrin, |
| 0.25 | part of cetyl polyglycol ether, |
| 3.50 | parts of polyethylene glycol, |
| 91 | parts of kaolin (particle size 0.3 – 0.8 mm). |

The active substance is mixed with epichlorohydrin and dissolved with 6 parts of acetone; the polyethylene glycol and cetyl polyglycol ether are then added. The solution thus obtained is sprayed on to kaolin, and the acetone is subsequently evaporated off in vacuo.

Wettable powder:

The following constituents are used in the preparation of (a) a 40%, (b) and (c) a 25%, and (d) a 10% wettable powder:

| | | |
|---|---|---|
| a) | 40 | parts of active substance, |
| | 5 | parts of sodium lignin sulphonate, |
| | 1 | part of sodium dibutyl-naphthalene sulphonate, |
| | 54 | parts of silicic acid; |
| b) | 25 | parts of active substance, |
| | 4.5 | parts of calcium lignin sulphonate, |
| | 1.9 | parts of Champagne chalk/hydroxyethyl cellulose mixture (1:1), |
| | 1.5 | parts of sodium dibutyl naphthalene sulphonate, |

-continued

| | | |
|---|---|---|
| | 19.5 | parts of silicic acid |
| | 19.5 | parts of Champagne chalk, |
| | 28.1 | parts of kaolin; |
| c) | 25 | parts of active substance, |
| | 2.5 | parts of isooctylphenoxy-polyoxyethylene-ethanol, |
| | 1.7 | parts of Champagne chalk/hydroxyethyl cellulose mixture (1:1), |
| | 8.3 | parts of sodium aluminium silicate, |
| | 16.5 | parts of kieselguhr, |
| | 46 | parts of kaolin; |
| d) | 10 | parts of active substance, |
| | 3 | parts of a mixture of the sodium salts of saturated fatty alcohol sulphates, |
| | 5 | parts of naphthalenesulphonic acid/formaldehyde condensate, |
| | 82 | parts of kaolin. |

The active substances are intimately mixed, in suitable mixers, with the additives; the mixture is then ground in the appropriate mills and rollers. Wettable powders are obtained which can be diluted with water to give suspensions of any desired concentration.

Emulsifiable concentrates:

The following substances are used to produce (a) a 10%, (b) a 25% and (c) a 50% emulsifiable concentrate:

| | | |
|---|---|---|
| a) | 10 | parts of active substance, |
| | 3.4 | parts of epoxidised vegetable oil, |
| | 3.4 | parts of a combination emulsifier consisting of fatty alcohol polyglycol ether and alkylarylsulphonate calcium salt, |
| | 40 | parts of dimethylformamide, |
| | 43.2 | parts of xylene; |
| b) | 25 | parts of active substance, |
| | 2.5 | parts of epoxidised vegetable oil, |
| | 10 | parts of alkylarylsulphonate/fatty alcohol-polyglycol ether mixture, |
| | 5 | parts of dimethylformamide, |
| | 57.5 | parts of xylene; |
| c) | 50 | parts of active substance, |
| | 4.2 | parts of tributylphenol-polyglycol ether, |
| | 5.8 | parts of calcium-dodecylbenzenesulphonate, |
| | 20 | parts of cyclohexanone, |
| | 20 | parts of xylene. |

It is possible to prepare from these concentrates, by dilution with water, emulsions of any desired concentration.

Spray:

The following constituents are used to produce (a) a 5% and (b) a 2% spray:

| | | |
|---|---|---|
| a) | 5 | parts of active substance, |
| | 1 | part of epichlorohydrin, |
| | 94 | parts of ligroin (boiling limits 160–190° C); and |
| b) | 2 | parts of active substance, |
| | 1 | part of Diazinon, |

-continued

| | |
|---|---|
| 97 | parts of kerosene. |

The following Examples serve to further illustrate the invention.

EXAMPLE 1

Production of O-ethyl-S-(n)-propyl-O-(2,3-diethoxycarbonyl-1-methyl-1-propenyl)-thiolphosphate of the formula

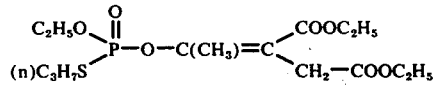

11.2 g of potassium-t-butylate is placed into 100 ml of acetonitrile, and 21.6 g of acetylsuccinic acid diethyl ester is added dropwise at 10°–20° C. There is subsequently added dropwise, also at 10°–20° C, 20.5 g of O-ethyl-S-(n)-propyl-thiochlorophosphate, and the reaction mixture is allowed to fully react overnight at room temperature. The salts are filtered off; the solvent is removed in vacuo and the residue is taken up in methylene chloride. The methylene chloride solution is successively washed with ice-cold diluted sodium hydroxide solution and with water, and afterwards concentrated in vacuo at 50° C. There is obtained 36.6 g of the product, O-ethyl-S-(n)-propyl-O-(2,3-diethoxycarbonyl-1-methyl-1-propenyl)-thiolphosphate (Compound No. 1) as a light-brown oil:
$n_D^{22} = 1.4809$: b.p. 0.001/145° C.

The following compounds of formula I are produced analogously:

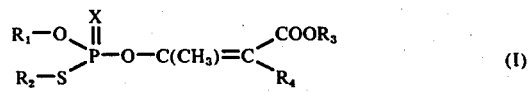

(I)

| Comp. No. | $R_1$ | $R_2$ | $R_3$ | $R_4$ | X | Physical data |
|---|---|---|---|---|---|---|
| 2 | $C_2H_5$— | $(n)C_3H_7$— | $C_2H_5$— | phenyl— | O | $n_D^{25}$: 1,5135; b.p. 0,001/150° C |
| 3 | $C_2H_5$— | $(n)C_3H_7$— | $C_2H_5$— | —$CH_2$—$COOC_2H_5$ | S | $n_D^{22}$: 1,5090 |
| 4 | $C_2H_5$— | $(n)C_3H_7$— | $CH_3$— | —$CH_2$—$COOCH_3$ | O | $n_D^{22}$: 1,4861 |
| 5 | $C_2H_5$— | (sec.) $C_4H_9$— | $C_2H_5$— | phenyl | O | $n_D^{22}$: 1,5132 |
| 6 | $C_2H_5$— | (iso)$C_3H_7$— | $C_2H_5$— | phenyl | O | $n_D^{20}$: 1,5142 |
| 7 | $CH_3$— | $(n)C_3H_7$— | $C_2H_5$— | —$CH_2$—$COOC_2H_5$ | O | $n_D^{24}$: 1,4871 |

-continued

| Comp. No. | $R_1$ | $R_2$ | $R_3$ | $R_4$ | X | Physical data |
|---|---|---|---|---|---|---|
| 8 | $C_2H_5-$ | (sec.)$C_4H_9-$ | $C_2H_5-$ | $-CH_2-COOC_2H_5$ | O | $n_D^{24}$: 1,4829 |
| 9 | $C_2H_5-$ | (iso)$C_3H_7-$ | $C_2H_5-$ | $-CH_2-COOC_2H_5$ | O | $n_D^{23}$: 1,4769 |
| 10 | $C_2H_5-$ | (iso)$C_5H_{11}-$ | $C_2H_5-$ | $-CH_2-COOC_2H_5$ | O | $n_D^{20}$: 1,4823 |
| 11 | $C_2H_5-$ | (n)$C_5H_{11}-$ | $C_2H_5-$ | $-CH_2-COOC_2H_5$ | O | $n_D^{22}$: 1,4805 |
| 12 | $C_2H_5-$ | (n)$C_3H_7-$ | (iso)$C_3H_7$ | $-CH_2-COOC_3H_7$(iso) | O | $n_D^{20}$: 1,4775 |
| 13 | $C_2H_5$ | (n)$C_3H_7-$ | benzyl | 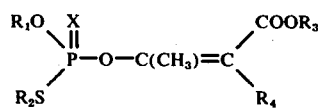 | O | $n_D^{20}$: 1,5395 |
| 14 | $C_2H_5-$ | (iso)$C_4H_9-$ | $C_2H_5-$ | $-CH_2-COOC_2H_5$ | O | $n_D^{22}$: 1,4792 |
| 15 | $C_2H_5-$ | (n)$C_3H_7-$ | $CH\equiv C-CH_2-$ | $-CH_2-COOC_2H_5$ | O | $n_D^{20}$: 1,4945 |
| 16 | $C_2H_5-$ | (n)$C_3H_7-$ | $C_2H_5-$ | $-CH_2-COOCH_2CH=CH_2$ | O | $n_D^{21}$: 1,5312 |
| 17 | $C_2H_5-$ | (n)$C_3H_7-$ | $\alpha-$phenethyl$-$ | $-CH_2-COOC_2H_5$ | O | $n_D^{21}$: 1,4390 |
| 18 | $C_2H_5-$ | (n)$C_3H_7-$ | $CH\equiv C-C(CH_3)_2-$ | $-CH_2-COOC_2H_5$ | O | $n_D^{21}$: 1,4922 |
| 19 | $C_2H_5-$ | (n)$C_3H_7-$ | $\beta-$phenethyl$-$ | $-CH_2-COOC_2H_5$ | O | $n_D^{21}$: 1,5155 |
| 20 | $C_2H_5-$ | (n)$C_3H_7-$ | (tert.)$C_4H_9-$ | $-CH_2-COOC_4H_9$(tert.) | O | $n_D^{20}$: 1,4756 |

EXAMPLE 2

A. Insecticidal stomach poison action

Cotton plants were sprayed with a 0.05% aqueous active-substance emulsion (obtained from a 10% emulsifiable concentrate).

After the drying of the resulting coating, Spodoptera littoralis larvae or Heliothis virescens larvae (both in the $L_3$ stage) were placed onto the plants. A percentage evaluation of the achieved mortality was made after 2, 4, 8, 24 and 48 hours. The test was carried out at 24° C with 60% relative humidity.

The compounds according to Example 1 exhibited in the above test a good insecticidal stomach poison action against Spodoptera littoralis and Heliothis virescens larvae. Compounds 1 to 5 are to be emphasised on account of their particularly good action (100% destruction in the case of both test species within 2 hours).

B. Insecticidal contact action

Broad beans (Vicia faba) grown in pots were infested, one day before application of the active substance, with about 200 bean aphids (Aphis fabae) per plant. Application to the leaves infested with aphids was effected by means of a compressed air spray using a spray emulsion at a concentration of 1000 ppm (produced from a 25% wettable powder).

An evaluation of the results obtained was made 24 hours after application.

The compounds according to Example 1 exhibited in the above test a good contact action on Aphis fabae.

EXAMPLE 3

Acaricidal action

Phaseolus vulgaris (bush beans) were infested, 12 hours before the test for acaricidal action, with an infested piece of leaf from a mass culture of Tetranychus urticae. The transferred mobile stages were sprayed with the emulsified test preparations from a chromatography-sprayer in a manner ensuring no running-off of the spray liquor. An assessment was made after 2 to 7 days, by examination under a binocular, of the living and of the dead larvae, adults and eggs, and the results were expressed as percentages. The treated plants were kept during the "holding time" in greenhouse compartments at 25° C.

Compounds according to Example 1 were effective in the above test against eggs, larvae and adults of Tetranychus urticae.

I claim:

1. Thio- and dithiophosphoric acid esters corresponding to the formula $$\begin{array}{c} R_1O \\ \diagdown \\ R_2S \end{array} \overset{X}{\underset{\|}{P}} -O-C(CH_3)=C \begin{array}{c} COOR_3 \\ \diagup \\ \diagdown \\ R_4 \end{array}$$

wherein
 $R_1$ is ethyl,
 $R_2$ is n-propyl,
 $R_3$ is methyl, ethyl or isopropyl,
 $R_4$ is phenyl, methoxycarbonylmethyl or ethoxycarbonylmethyl, and
 X is oxygen or sulphur.

2. O-Ethyl-S-(n)-propyl-O-(2,3-diethoxycarbonyl-1-methyl-1-propenyl)-thiolphosphate according to claim 1.

3. O-Ethyl-S-(n)-propyl-O-(2,3-diethoxycarbonyl-1-methyl-1-propenyl)-dithiophosphate according to claim 1.

4. O-Ethyl-S-(n)-propyl-O-(2,3-dimethoxycarbonyl-1-methyl-1-propenyl)-thiolphosphate according to claim 1.

5. O-Ethyl-S-(n)-propyl-O-(1-ethoxy-carbonyl-1-phenyl-1-propen-2-yl)-thiolphosphate according to claim 1.

6. A composition for the control of insects and members of the order Acarina, which composition comprises an insecticidally or acaricidally effective amount of a thio- or dithiophosphoric acid ester as claimed in claim 1, together with a suitable carrier therefor.

7. A method for combatting pests of the class Insecta or of the order Acarina which comprises applying to said pests or their locus an insecticidally or acaricidally effective amount of a thio- or dithiophosphoric acid ester as claimed in claim 1.

* * * * *